(12) United States Patent
Atlas (10) Patent No.: US 7,625,366 B2
(45) Date of Patent: *Dec. 1, 2009

(54) FLUSH CATHETER WITH FLOW DIRECTING SHEATH

(75) Inventor: Michael Atlas, Arlington, MA (US)

(73) Assignee: Lightlab Imaging, LLC, Westford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/822,600

(22) Filed: Jul. 9, 2007

(65) Prior Publication Data

US 2007/0260198 A1 Nov. 8, 2007

Related U.S. Application Data

(63) Continuation of application No. 10/423,016, filed on Apr. 25, 2003, now Pat. No. 7,241,286.

(51) Int. Cl.
*A61M 25/00* (2006.01)
*A61N 1/30* (2006.01)
*A61B 1/12* (2006.01)
*A61B 6/00* (2006.01)

(52) U.S. Cl. .................. 604/537; 604/21; 600/156; 600/478

(58) Field of Classification Search .................. 604/523, 604/537, 539, 20–22, 103.04, 164.01, 164.08, 604/171, 246, 247, 266, 267; 600/155–158, 600/153

See application file for complete search history.

(56) References Cited

U.S. PATENT DOCUMENTS

| 4,878,893 | A | | 11/1989 | Chin |
| 5,321,501 | A | | 6/1994 | Swanson et al. |
| 5,425,723 | A | * | 6/1995 | Wang ........................ 604/523 |
| 5,459,570 | A | | 10/1995 | Swanson et al. |
| 5,464,404 | A | * | 11/1995 | Abela et al. ................... 606/15 |
| 5,465,147 | A | | 11/1995 | Swanson |
| 5,748,598 | A | | 5/1998 | Swanson et al. |
| 5,784,352 | A | | 7/1998 | Swanson et al. |
| 5,956,355 | A | | 9/1999 | Swanson et al. |
| 6,111,645 | A | | 8/2000 | Tearney et al. |
| 6,134,003 | A | | 10/2000 | Tearney et al. |
| 6,160,826 | A | | 12/2000 | Swanson et al. |
| 6,191,862 | B1 | | 2/2001 | Swanson et al. |
| 6,282,011 | B1 | | 8/2001 | Tearney et al. |
| 6,421,164 | B2 | | 7/2002 | Tearney et al. |
| 6,445,939 | B1 | | 9/2002 | Swanson et al. |
| 6,485,413 | B1 | | 11/2002 | Boppart |

(Continued)

*Primary Examiner*—Kevin C Sirmons
*Assistant Examiner*—Andrew M Gilbert
(74) *Attorney, Agent, or Firm*—K&L Gates LLP (57) ABSTRACT

A flush catheter is provided which is configured to be introduced into an orifice to create a flush zone therein. The flush catheter includes a catheter body having an inner cavity, the inner cavity being configured to communicate with a source of flush solution, one or more openings configured to expel therethrough flush solution, and a sheath at least partially covering the one or more openings, wherein when flush solution is expelled through the one or more openings, the flush solution is directed by the sheath to flow along an outer surface of the catheter body, thereby creating a flush zone along a length of the outer surface of the catheter body. The flush catheter may be used in combination with an image catheter/probe such as an image catheter/probe utilized in OCT imaging systems.

20 Claims, 4 Drawing Sheets

U.S. PATENT DOCUMENTS

| | | |
|---|---|---|
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,783,522 B2* | 8/2004 | Fischell ............... 604/537 |
| 6,879,851 B2 | 4/2005 | McNamara et al. |
| 6,891,984 B2 | 5/2005 | Petersen et al. |
| 7,241,286 B2* | 7/2007 | Atlas ............... 604/537 |
| 2002/0016564 A1* | 2/2002 | Courtney et al. ......... 604/96.01 |
| 2002/0161351 A1* | 10/2002 | Samson et al. ............... 604/507 |
| 2004/0176742 A1* | 9/2004 | Morris et al. ............... 604/537 |
| 2004/0215166 A1 | 10/2004 | Atlas |
| 2005/0201662 A1 | 9/2005 | Petersen et al. |
| 2006/0095065 A1 | 5/2006 | Tanimura et al. |
| 2006/0241503 A1 | 10/2006 | Schmitt et al. |
| 2007/0260198 A1 | 11/2007 | Atlas |
| 2008/0161696 A1 | 7/2008 | Schmitt et al. |
| 2008/0165366 A1 | 7/2008 | Schmitt et al. |

\* cited by examiner

FLUSH CATHETER WITH FLOW DIRECTING SHEATH

REFERENCE TO RELATED APPLICATIONS

This application is a continuation of U.S. patent application Ser. No. 10/423,016, filed on Apr. 25, 2003, now U.S. Pat. No. 7,241,286, the disclosure of which is incorporated by reference herein in its entirety.

BACKGROUND OF THE INVENTION

1. Field of the Invention

The invention is directed to a flush catheter and, more particularly, to a flush catheter provided with a flow directing sheath.

2. Background of the Related Art

In order to obtain clear in-vivo images of arterial walls when using, for example, Optical Coherence Tomography (OCT), it is necessary to displace blood from a cylindrical volume around a tip of an imaging probe. To allow surveying of a length of an artery wall, it is desirable that the cylindrical volume be, for example, as long as approximately 40-50 mm or more. The better the blood is cleared from this volume, the better the image obtained of the arterial wall.

For example, in almost all uses of OCT for imaging during cardiac cauterizations, an imaging probe disposed within a guide catheter is inserted into an artery such that a direction of blood flow is from a proximal end of the imaging probe toward a distal end of the catheter or probe. It is desirable that a location of the cleared cylindrical volume be somewhat proximal to the distal end of the catheter, to allow the use of a "minirail" delivery system. A "minirail" delivery system utilizes a guide wire and a flexible tip attachable to the imaging probe. The guide wire is used to guide the imaging probe into the desired artery.

Previous and current methods of achieving the desired cleared volume or blood displacement have included the use of cardiac dilation balloons, the injection of saline through a guide catheter, and the injection of saline through a selective flush catheter inserted over the imaging catheter. All three of these methods provide less than ideal solutions.

The balloon method either involves total occlusion of a vessel for the time that the image is desired, or the use of under-inflated balloons which does not completely remove the blood from the field of view. The guide flush method requires a large flow rate of saline that can over hydrate the patient. This method is also very ineffective when side branches are present.

For example, when blood flow is from a proximal to a distal end of the imaging probe, the selective flush catheter method has the inherent limitation that blood from the area proximal to the flush point is entrained into the flush solution at a point where the flush solution exits the catheter. Increasing the flow rate of flush solution tends to entrain more blood, making it difficult to dilute the blood enough to provide a clear imaging area. In addition, it is difficult to configure this type of device for a minirail delivery system.

U.S. Pat. No. 4,878,893 (hereinafter "the 893 patent") to Albert K. Chin entitled AAngioscope with Flush Solution Deflector Shield,@ which is hereby incorporated by reference, provides a partial solution to this problem, and is intended for use with an angioscope catheter. The 893 patent teaches the use of a curved deflector shield 30 bonded to a distal tip of a catheter 10. The deflector shield 30:

Ycauses the flushing solution to momentarily flow against blood flow toward the proximal end of the catheter. The blood flow will then carry the solution back past the distal tip of the angioscope 18, as shown in FIG. 13 [of the 893 patent] to provide the bolus required for clear visualization as discussed at col. 5, lines 1-6, of the 893 patent. However, the approach of the '893 patent has several deficiencies which prevent its use in an OCT application and which make it difficult to produce.

For example, the deflector shield must be at a distal end of the catheter, making it difficult to use a minirail type of delivery system. Further, the design does not strongly direct the flushing solution in an axial proximal direction. This results in much of the flushing solution moving out from the catheter in a radial direction. As such, the bolus of flushing solution does not flow very far toward the proximal end of the catheter and will not provide the long volume desirable for surveying a length of the artery wall. Furthermore, radially directed jets of fluid can damage the sensitive endothelial layer of the vessel and could even perforate the vessel.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

The invention is directed to a flush catheter, and more particularly, to a flush catheter with a flow directing sheath.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The invention is directed to a flush catheter configured to be inserted into an artery, vessel, or other orifice in a patient. The flush catheter includes a catheter body, having a hollow inner cavity. The inner cavity is configured to communicate with a source of flush solution. The flush solution used may be, for example, sterile physiological saline, pure contrast solution, or a mixture of sterile saline and angiographic contrast solution. Other fluids may also be appropriate based on the particular application. One or more openings may be formed in an outer surface of the catheter body and may be arranged radially around a periphery of the catheter body in one or more rows.

The flush catheter further includes a sheath. According to one embodiment of the invention, the sheath can be formed of a thin piece of material of slightly larger inner diameter than an outer diameter of the catheter body. The sheath is positioned over the one or more openings and may be attached to the catheter body with an attaching means. In one embodiment, the sheath is attached to the catheter body at only one end, thus creating an annular volume open at the other end and extending along a length of the catheter body. In one embodiment, the sheath is attached to the catheter body at one end creating an annular volume open on an end facing a proximal end of the catheter when inserted into an artery, vessel, or other orifice, and extending along a length of the catheter body.

The flush catheter according to the invention may include a minirail delivery system at a distal end. In the case of a minirail delivery system, the one or more holes would be positioned a distance proximal to where the minirail attaches to the flush catheter.

For use with humans or animals, the sheath is preferably formed of a biocompatible material. For OCT or other imaging applications, the sheath is preferably transparent to allow light or other electromagnetic radiation to pass therethrough. In one embodiment, the sheath is formed of transparent polyethylene terephthalate (PET), although other materials may be appropriate based on the particular application.

Upon operation, the flush catheter is introduced into an artery, vessel, or other orifice of a patient. Flush solution provided by a flush solution source in communication with the inner cavity is directed through the inner cavity and radially outward through the one or more openings. The flush solution is then directed axially along an outer surface of the catheter body by the flow directing sheath.

That is, the flush solution introduced into the catheter from the proximal end flows radially out of the holes and is directed by the sheath along the outer surface of the flush catheter in a proximal direction. As the flush solution interacts with the blood flowing from the proximal end to the distal end of the flush catheter, it spreads out in the artery, vessel, or other bodily cavity or orifice, effectively substantially clearing a volume of the artery, vessel, or other bodily cavity or orifice.

For example, in the case of a blood vessel, by using an appropriate amount of flush solution an entire cylindrical volume may be substantially cleared of blood, using a flush flow rate significantly less than the flow rate of blood in the vessel. The ability to substantially clear a vessel of blood in an extended area while using a minimal rate of flush solution is one of the advantages of the invention.

The size and location of the one or more openings relative to an open end of the sheath may be chosen to allow for a substantially radially uniform flow of the flush solution from the sheath. By varying an inner diameter of the sheath and/or the catheter, a thickness of the annular gap may be modified, allowing for an average axial velocity of the flush solution to be controlled for a given flush flow rate.

By doing this, the momentum of the flush solution (proportional to Average Velocity×Mass Flow Rate of the flush solution) leaving the sheath may be varied to counteract the momentum of the blood flowing in the vessel. By raising the average velocity of the flush solution, a smaller mass flow rate can still counteract a larger but slower moving mass flow rate of blood. By varying the gap between the sheath and flush catheter, the momentum of the flush solution can be tuned to give the optimal length of cleared volume proximal to the sheath for a given application while using a minimal amount of flush solution.

Because all of the flush solution leaves the flush catheter in an axial direction, there is little worry of producing damage to the arterial or vessel wall. In addition, the proximity of the flush solution flow to the outer surface of the flush catheter substantially clears the outer surface of blood.

A specific embodiment of a flush catheter according to the invention will now be discussed in detail below. The following discussion teaches using the flush catheter in combination with an imaging catheter/probe, such as an image catheter/probe associated with an OCT device. However, the invention can be applied to other applications for which controlled flushing of an area is desirable.

Further, the flush catheter of FIGS. 1-7 is shown used with a minirail delivery system. However, other delivery systems may also be appropriate.

Figure 1:
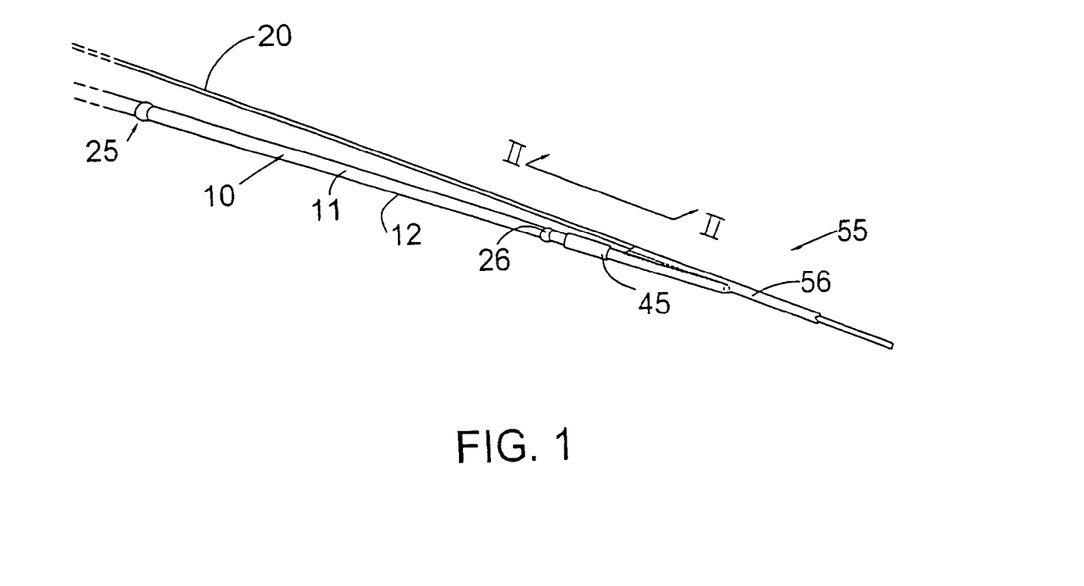
FIG. 1 is a schematic, partial, side, perspective view of a flush catheter implemented in combination with an imaging probe according to an embodiment of the invention.
Figure 2:
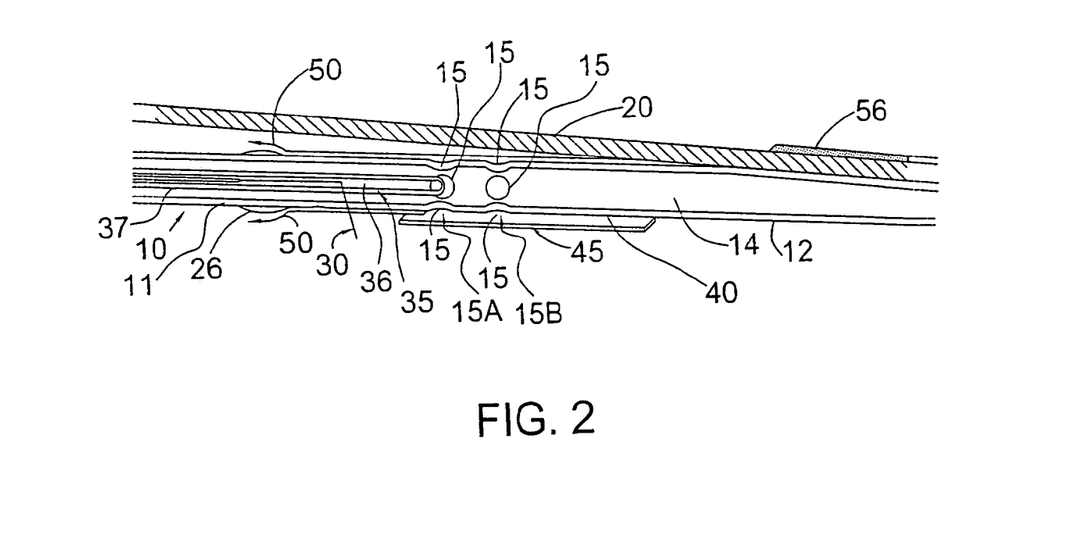
FIG. 2 is a schematic, partial, side, cross-sectional view of the flush catheter implemented in combination with an imaging probe of FIG. 1.
Figure 3:
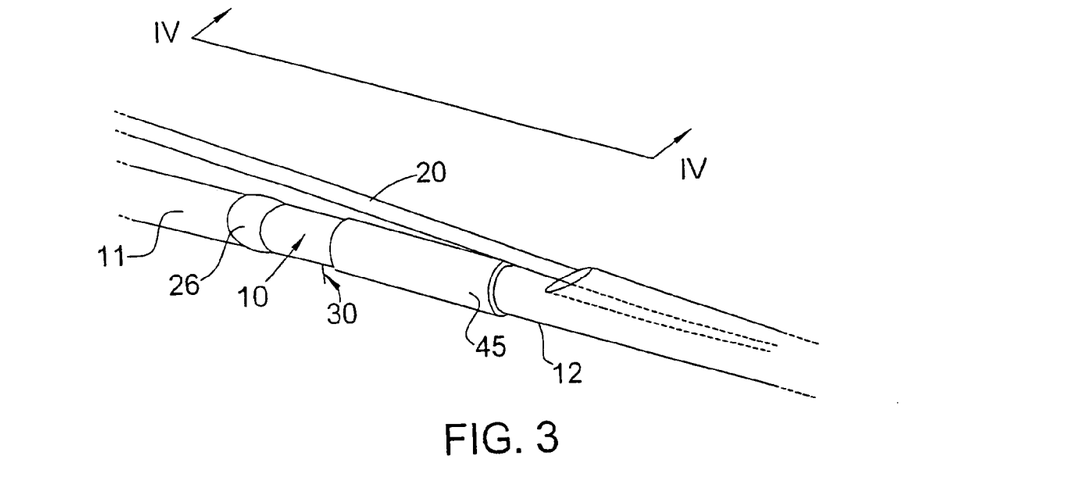
FIG. 3 is another schematic, partial, side, perspective view of the flush catheter implemented in combination with an imaging probe of FIG. 1.
Figure 4:
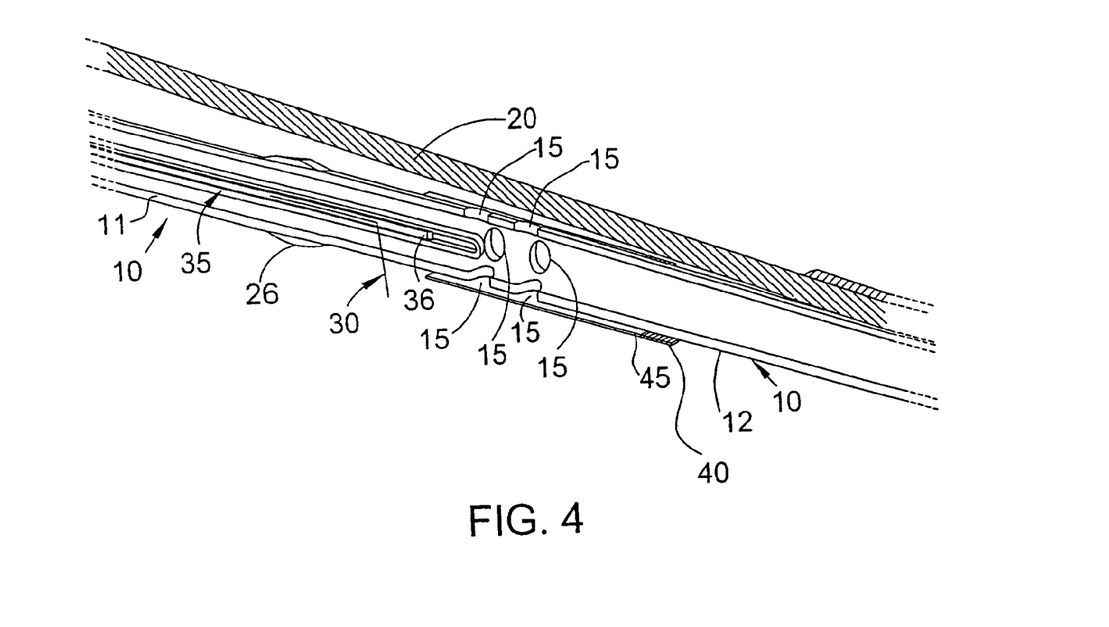
FIG. 4 is another schematic, partial, side, cross-sectional perspective view of the flush catheter implemented in combination with an imaging probe of FIG. 1.
Figure 5:
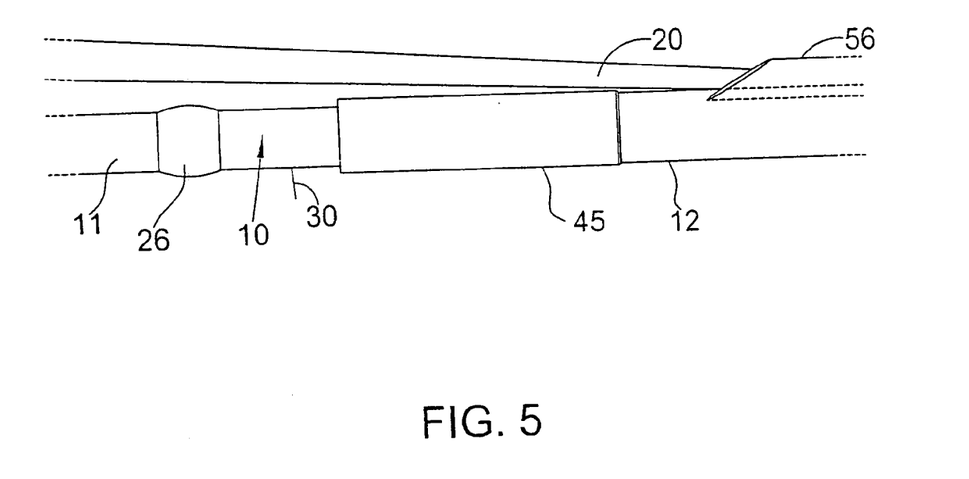
FIG. 5 is a schematic, partial, side view of the flush catheter implemented in combination with an imaging probe of FIG. 1.
Figure 6:
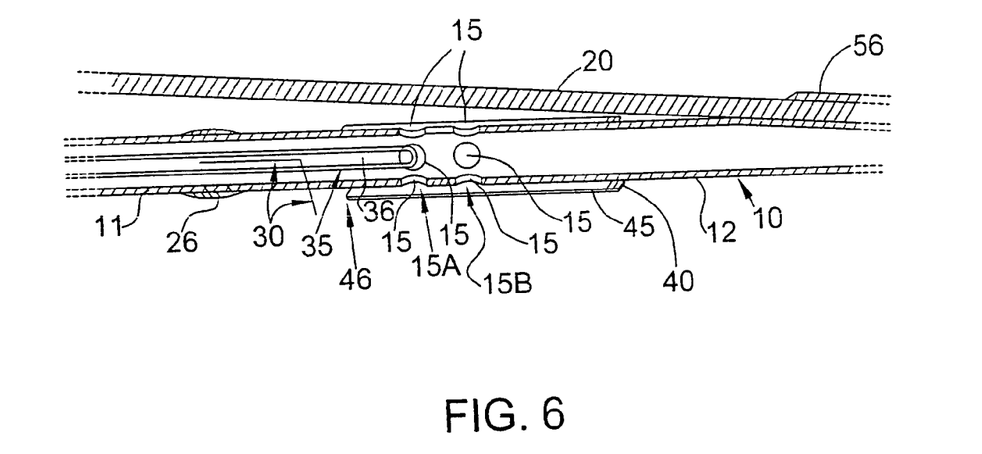
FIG. 6 is a schematic, partial, side, cross-sectional view of the flush catheter implemented in combination with an imaging probe of FIG. 1.
Figure 7:
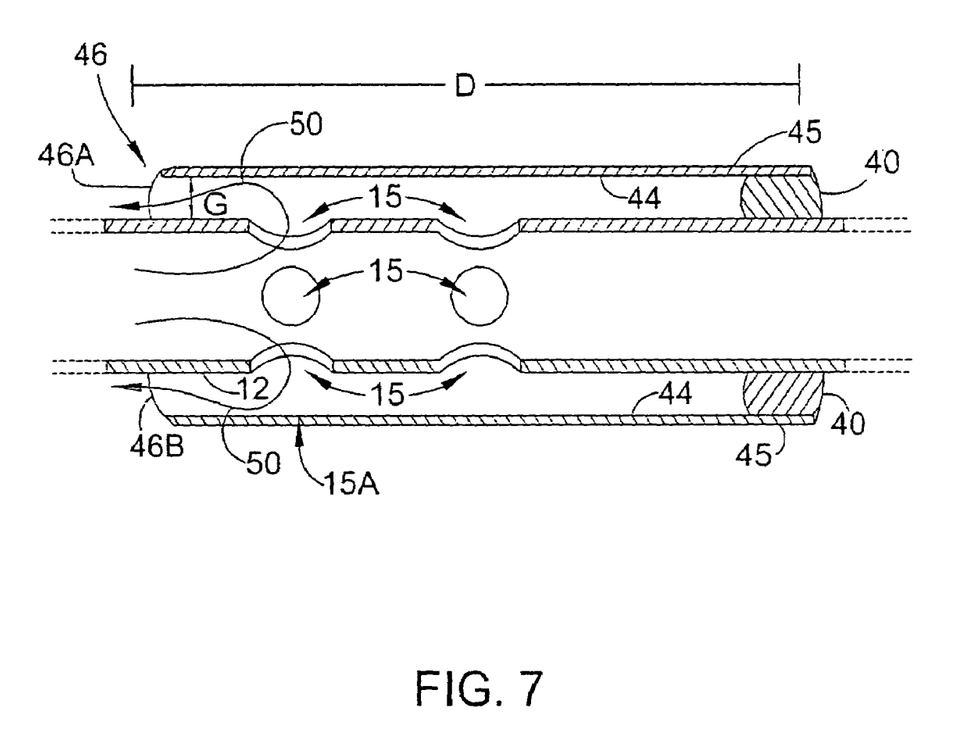
FIG. 7 is an enlarged, schematic, side, cross-sectional view of the sheath according to the invention.

FIG. 1 is a schematic, partial, side, perspective view of a flush catheter implemented in combination with an imaging probe according to an embodiment of the invention. FIG. 2 is a schematic, partial, side, cross-sectional view of the flush catheter implemented in combination with an imaging probe of FIG. 1. FIG. 3 is another schematic, partial, side, perspective view of the flush catheter implemented in combination with an imaging probe of FIG. 1. FIG. 4 is another schematic, partial, side, cross-sectional perspective view of the flush catheter implemented in combination with an imaging probe of FIG. 1. FIG. 5 is a schematic, partial, side view of the flush catheter implemented in combination with an imaging probe of FIG. 1. FIG. 6 is a schematic, partial, side, cross-sectional view of the flush catheter implemented in combination with an imaging probe of FIG. 1. FIG. 7 is an enlarged, schematic, side, cross-sectional view of the sheath according to the invention.

FIG. 1 shows a flush catheter assembly 1 comprising a flush catheter 10. In the embodiment of FIG. 1, the flush catheter 10 is shown used in combination with a minirail delivery system 55. The minirail delivery system 55 includes a flexible tip 56 provided as part of the flush catheter 10 or configured to attach to the flush catheter 10, removably or permanently. The flexible tip 56 is configured to receive a guide wire 20, as shown in FIG. 1. The guide wire 20 allows the flush catheter 10 to be guided into an artery, vessel or other bodily cavity or orifice by a surgeon or other user.

For OCT imaging use, it is preferable that the flush catheter be made of a material that is transparent to the wavelengths of light used. For use with humans or animals, it is preferably that the flush catheter be made of a material that is biocompatible. One appropriate material that is both transparent and biocompatible is clear thermoplastic, one example of which is Polyester Block Amide, known as PEBA. However, other materials may also be appropriate.

The flush catheter 10 includes a catheter body 11 having an inner cavity 14. The inner cavity 14 is configured to communicate with a source of flush solution (not shown). The flush solution used may be, for example, sterile physiological saline, pure contrast solution, or a mixture of sterile saline and angiographic contrast solution. Other fluids may also be appropriate based on the particular application.

The inner cavity 14 is configured to receive an imaging core 35. The imaging core 35 includes an outer casing 37 in which an imaging probe 36, for example, a wire or optical fiber, is disposed. The imaging probe 36 is designed to output a beam of light 30 radially. The beam of light extends down a length of the imaging probe 36 and is deflected radially by a mirror 38. The imaging probe 36 may be rotated within the imaging core 35 to provide a disk-like scan of a target, such as an inner wall of an artery, vessel, or other bodily cavity or orifice. The imaging probe 36 may then be pulled lengthwise to scan a length of the target. That is, the imaging core 35 may be moved axially between a position underneath the flush sheath 45 proximal a distal marker band 26 to the proximal marker band 25. In this way, a survey may be made of a length of the wall of the artery, vessel, or other bodily cavity or orifice.

The imaging core 35 and imaging probe 36 are both preferably formed of a transparent material to allow the light beam 30 to pass therethrough. For example, the imaging core may be formed of polyester block amide, known as PEBA, onylon and the imaging probe may be formed of, for example, silica glass. However, other materials may also be appropriate.

As mentioned above, the flush catheter 10 further includes distal and proximal marker bands 25, 26, which may be raised as in the embodiment of FIG. 1. The marker bands 25, 26 are configured to allow a user to control the position of the flush catheter 10 and/or imaging probe 36. For example, the marker bands may be configured to be visible on, for example, an angiogram and may be used to find the position of the catheter in, for example, an arterial system. Also, if the marker bands are opaque to the O.C.T. probe, they provide a reference during pullbacks.

The flush catheter further includes one or more openings 15, as shown in FIG. 2, disposed in the catheter body 11. The one or more openings may be formed in an outer surface 12 of the catheter body 11 and may be arranged radially around a periphery of the catheter body 10 in one or more rows 15A, 15B.

Further, the flush catheter 10 further includes a sheath 45. The sheath 45 at least partially covers the one or more openings 15. The sheath 45 may comprise a thin piece of material and may be in the form of a cylinder disposed around the outer surface 12 of the catheter body 11 and extending a predetermined distance D along the length of the catheter body, as shown in FIG. 7.

The sheath 45 may be attached to an outer surface 12 of the flush catheter 10 by an attaching means 40, such as an adhesive. In one embodiment, the sheath is attached to the catheter body 11 at one end creating an annular volume open on an end facing a proximal end of the catheter 10 when inserted into an artery, vessel, or other bodily cavity or orifice. A gap G is formed between the inner surface 44 of the sheath 45 and the outer surface 12 of the catheter body 11.

In operation, the flush solution from a source (not shown) is pumped into and through inner cavity 14 and is expelled through opening(s) 15. The flush solution expelled through opening(s) 15 is directed by sheath 45 to flow along the outer surface 12 of the flush catheter 10, as shown by reference numeral 50 in FIGS. 2 and 7, forming a flush zone extending from the opening(s) 15 along the outer surface 12 of the flush catheter 12 to at least the distal marker band 25.

By varying a distance of the gap G formed between the sheath 45 and the opening(s) 15, the flow 50 can be controlled. That is, flush solution introduced into the flush catheter 10 from the proximal end flows radially out of the opening(s) 15 and is directed by the sheath 45 along the outer surface 12 of the flush catheter 10 in a proximal direction. The flush solution leaves the sheath 45 moving axially in a proximal direction. As the flush solution interacts with blood and/or other matter coming from the proximal to the distal end it will begin to spread out in the artery, vessel, or other bodily cavity or orifice, effectively substantially clearing a volume of the artery, vessel, or other bodily cavity or orifice of blood and/or other matter. The distal and/or proximal marker bands 25, 26 may be contoured to avoid blocking the flow of the flush solution along the outer surface 12 of the flush catheter 10. In addition, the distal and/or proximal marker bands 25, 26 may be sized to effectively prevent open edges 46A, 46B of the sheath 45 from contacting the walls of the artery, vessel, or other bodily cavity or orifice, minimizing the chances of damage when moving the entire flush catheter in a proximal direction.

By using an appropriate amount of flush solution, an entire cylindrical volume between the two marker bands 25, 26 may be substantially cleared of blood and/or other matter creating a flush zone, using a flush flow rate significantly less than the flow rate of blood in the artery, vessel, or other bodily cavity or orifice. The ability to substantially clear an artery, vessel, or other bodily cavity or orifice of blood and/or other matter in an extended area while using a minimal rate of flush solution is one of the advantages of the invention.

The size and location of the opening(s) 15 relative to the open end 46 of the sheath 45 may be chosen to allow for a substantially radially uniform flow of the flush solution from the sheath 45. By varying an inner diameter of the sheath 45 and/or the flush catheter 10, a thickness of the annular gap G may be modified, allowing for an average axial velocity of the flush solution to be controlled for a given flush flow rate. By doing this, the momentum of the flush solution (proportional to Average Velocity×Mass Flow Rate of the flush solution) leaving the sheath 45 may be varied to counteract the momentum of the blood and/or other matter flowing in the artery, vessel, or other orifice. By raising the average velocity of the flush solution, a smaller mass flow rate can still counteract a larger but slower moving mass flow rate of blood and/or other matter. By varying the gap G between the sheath 45 and flush catheter 10, the momentum of the flush solution can be tuned to give the optimal length of cleared volume proximal to the sheath 45 for a given application while using a minimal amount of flush solution.

Because all of the flush solution leaves the flush catheter 10 in an axial direction, there is little worry of producing damage to the walls of the artery, vessel, or other bodily cavity or orifice. In addition, the proximity of the flush solution flow to the outer surface 12 of the catheter 10 substantially clears the outer surface 12 of blood and/or other matter, resulting in a substantially clear image produced by the imaging probe 36.

Although the details of the flush catheter according to the invention have been optimized for its use in an OCT application, it is obvious that it may be easily modified for use in other applications, in particular where a complete flush is desired while using a minimum amount of flush solution.

Further, the design allows the flush zone to be placed anywhere along the flush catheter, merely by moving the positions of the opening(s) 15 and sheath 45. In applications where the flush catheter is introduced in the opposite direction, i.e. blood flow is toward a distal end of the flush catheter, the sheath may be reversed to provide effective flushing.

Further, by varying the gap between the sheath and the flush catheter, the average velocity of the flush solution leaving axially from the sheath may be controlled for a given flush rate. Additionally, by varying the number, size, and location of the opening(s) relative to the open end of the sheath, substantially non-uniform flows may be achieved for special applications.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A flush catheter configured to be introduced into a lumen to create an optically transparent flush zone, comprising:
   a catheter body having a non-occlusive distal end configured to be introduced into a lumen and an inner cavity, the inner cavity being configured to communicate with a proximal source of contrast solution and expel the contrast solution at a distal end of the catheter;
   an image probe assembly contained within the catheter body;
   one or more openings provided in the catheter body configured to expel therethrough contrast solution; and
   a sheath at least partially covering the one or more openings, wherein a circumferential gap exists between the sheath and a catheter body, wherein when contrast solution is expelled through the one or more openings into the gap, the contrast solution is directed by the sheath to flow along an outer surface of the catheter body toward a proximal end of the catheter body, and wherein a contrast solution flow rate and the gap are configured such that a volume flow rate of the expelled contrast solution is substantially equivalent but opposite to that of locally flowing blood thereby creating the optically transparent flush zone along a length of the outer surface of the catheter body between the outer surface of the catheter body and an inner surface of the lumen such that non-occlusive optical imaging of the lumen can be performed by the image probe assembly.

2. The flush catheter of claim 1, wherein a distance between the outer surface of the catheter body and an inner surface of the sheath determines an average axial velocity of the contrast solution for a given contrast solution flow rate.

3. The flush catheter of claim 1, wherein the sheath comprises a thin piece of material in the form of a cylinder disposed around the catheter body, and wherein the sheath extends a predetermined distance along a length of the catheter body.

4. The flush catheter of claim 3, wherein the sheath is attached to the catheter body by an attaching means at one end thereof.

5. The flush catheter of claim 4, wherein the attaching means is an adhesive.

6. The flush catheter of claim 1, wherein the sheath is formed of a biocompatible material.

7. The flush catheter of claim 1, wherein a position of the one or more openings and the sheath determine a position of the optically transparent flush zone.

8. The flush catheter of claim 1, wherein the one or more openings are formed in the outer surface of the catheter body.

9. The flush catheter of claim 8, wherein the one or more openings comprise a plurality of openings arranged radially around the catheter body.

10. The flush catheter of claim 9, wherein the plurality of openings are arranged in one or more rows arranged radially around the catheter body.

11. A flush catheter configured to be introduced into a narrow, blood-carrying bodily lumen, the flush catheter comprising:
   a catheter body having a non-occlusive distal end configured to be introduced into a lumen and a proximal end and a first inner cavity extending from the proximal end to the distal end, the inner cavity being configured to communicate with a proximal source of contrast solution;
   a second inner cavity located at the distal end of the catheter body configured to accept a guidewire for guiding the flush catheter to a point of interest in the bodily lumen;
   one or more openings in communication with the first cavity configured to expel the contrast solution; and
   a sheath covering the one or more openings, wherein the sheath is sealed to an outer catheter wall of the catheter body at a distal end thereof adjacent to the one or more openings and unattached at a proximal end thereof such that a circumferential gap is formed between the sheath covering and the catheter body,
   wherein the sheath is configured to direct contrast solution expelled through the one or more openings into the gap to flow along the outer wall of the catheter body in a direction retrograde to flow of contrast solution in the first cavity and exit the sheath at its proximal end; and an imaging probe assembly disposed inside the first cavity,
   wherein a flush rate of the expelled contrast solution and the gap are configured such that a volume flow rate of the expelled contrast solution is substantially equivalent but opposite to that of locally flowing blood, thereby displacing a region of blood proximal to the proximal end of the sheath and creating an optically transparent region between the outer wall of the catheter body and an inner wall of the bodily lumen such that non-occlusive optical imaging of the bodily lumen can be performed by the imaging probe assembly.

12. The flush catheter of claim 11, wherein a distance between the outer wall of the catheter body and an inner surface of the sheath determines an average axial velocity of the contrast solution for a given contrast solution flow rate.

13. The flush catheter of claim 11, wherein the sheath comprises a thin piece of material in the form of a cylinder disposed around the catheter body, and wherein the sheath extends a predetermined distance along a length of the catheter body.

14. The flush catheter of claim 13, wherein the sheath is sealed to the catheter body by an attaching means at the distal end thereof.

15. The flush catheter of claim 14, wherein the attaching means is an adhesive. pg,19

16. The flush catheter of claim 11, wherein a position of the one or more openings and the sheath determine a position of the optically transparent region.

17. The flush catheter of claim 11, wherein the one or more openings are formed in the outer wall of the catheter body.

18. The flush catheter of claim 17, wherein the one or more openings comprise a plurality of openings arranged radially around the catheter body.

19. The flush catheter of claim 18, wherein the plurality of openings are arranged in one or more rows arranged radially around the catheter body.

20. The flush catheter of claim 11, wherein the contrast solution is selected from the group consisting of a pure contrast solution, an angiographic contrast solution, and a mixture of angiographic contrast solution and saline.

* * * * *